United States Patent
Kulprathipanja et al.

(10) Patent No.: US 7,368,618 B2
(45) Date of Patent: May 6, 2008

(54) PROCESS FOR REMOVAL OF OXYGENATES FROM A PARAFFIN STREAM

(75) Inventors: Santi Kulprathipanja, Inverness, IL (US); James W. Priegnitz, Elgin, IL (US); Stephen W. Sohn, Arlington Heights, IL (US); Bryan K. Glover, Algonquin, IL (US); Bipin V. Vora, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 16 days.

(21) Appl. No.: 11/457,889

(22) Filed: Jul. 17, 2006

(65) Prior Publication Data

US 2006/0247481 A1 Nov. 2, 2006

Related U.S. Application Data

(60) Division of application No. 10/882,887, filed on Jun. 30, 2004, now Pat. No. 7,102,044, which is a continuation-in-part of application No. 10/739,765, filed on Dec. 18, 2003, now abandoned, which is a continuation-in-part of application No. 10/318,599, filed on Dec. 12, 2002, now abandoned.

(51) Int. Cl.
C07C 5/327 (2006.01)

(52) U.S. Cl. ..................................................... 585/264
(58) Field of Classification Search ................. 585/264
See application file for complete search history.

(56) References Cited

U.S. PATENT DOCUMENTS

| | | | | |
|---|---|---|---|---|
| 2,448,489 A | 8/1948 | Hirschler | ..................... | 260/674 |
| 2,531,324 A | 11/1950 | Cope et al. | .................. | 260/450 |
| 2,882,244 A | 4/1959 | Milton | ........................ | 252/455 |
| 3,931,350 A | 1/1976 | Sparks | .................... | 260/671 B |
| 4,404,118 A | 9/1983 | Herskovits | .............. | 252/411 R |
| 4,973,453 A | 11/1990 | Agee | .......................... | 422/190 |
| 5,427,689 A | 6/1995 | Kallenbach et al. | ......... | 210/670 |
| 6,111,162 A | 8/2000 | Rossini et al. | .............. | 585/824 |
| 6,225,518 B1 | 5/2001 | Sohn et al. | ................. | 585/826 |

*Primary Examiner*—Thuan Dinh Dang
(74) *Attorney, Agent, or Firm*—Mark Goldberg

(57) ABSTRACT

The present invention comprises a process for removal of oxygenates from a paraffin-rich or olefin-rich paraffin stream which comprises passing a feed stream, comprising one or more $C_{10}$ to $C_{15}$ feed paraffins or $C_{10}$ to $C_{15}$ olefin-rich paraffin stream and one or more oxygenates through an adsorbent bed comprising one or more adsorbents selected from silica gel, activated alumina and sodium x zeolites to remove essentially all of said oxygenates; and recovering said paraffins. A second adsorbent bed may be employed to more thoroughly remove these oxygenates.

3 Claims, 4 Drawing Sheets

PROCESS FOR REMOVAL OF OXYGENATES FROM A PARAFFIN STREAM

CROSS-REFERENCE TO RELATED APPLICATIONS

This application is a Division of application Ser. No. 10/882,887 filed Jun. 30, 2004 now U.S. Pat. No. 7,102,044, which in turn is a Continuation-In-Part of application Ser. No. 10/739,765 filed Dec. 18, 2003, now abandoned, which in turn is a Continuation-In-Part of application Ser. No. 10/318,599 filed Dec. 12, 2002, now abandoned, the contents of which are hereby incorporated by reference in its entirety.

BACKGROUND OF THE INVENTION

This invention relates to a process for removing oxygenates from paraffins or paraffin and olefin mixture. This invention is in particular useful in removal of oxygenates from $C_{10}$ to $C_{15}$ paraffins or a mixture of paraffins and olefins prior to use of these paraffins or olefins or mixtures thereof in further processes or reactions.

There are a number of industrial applications for paraffins or olefins or mixtures thereof in the $C_{10}$ to $C_{15}$ range. Among these uses are as a precursor to linear alkylbenzene benzene (LAB) which is used to produce linear alkylbenzene sulfonate (LAS), the workhorse surfactant of the detergent industry. These paraffins or olefins or mixtures thereof can also be used as precursors to be upgraded to higher value fuels. As concerns over pollution caused by traditional fossil fuels increase and as sources of crude oil decrease, there has been increased interest in other sources of energy. One promising source of energy is the synthetic production of fuels, lubricants and other products from natural gas or coal. The gas to fuels process is often referred to as gas-to-liquids or GTL and is often made by the Fischer-Tropsch process. See for example, U.S. Pat. No. 4,973,453, which is incorporated by reference herein. The linear paraffins and olefins in the $C_{10}$ to $C_{15}$ range are of particular value in connection with these processes.

The synthetic production of hydrocarbons by the catalytic reaction of synthesis gas is well known and is generally referred to as the Fischer-Tropsch reaction. The Fischer-Tropsch process was developed in early part of the 20$^{th}$ century in Germany. It was practiced commercially in Germany during World War II and later has been practiced in South Africa.

Synthesis gas (primarily hydrogen and carbon monoxide) is produced from coal or natural gas (methane). Then the synthesis gas is converted to liquid hydrocarbons. The Fischer-Tropsch reaction for converting synthesis gas has been characterized in some instances by the following general reaction:

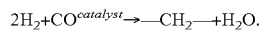

$2H_2 + CO \xrightarrow{catalyst} —CH_2— + H_2O$.

The hydrocarbon products derived from the Fischer-Tropsch reaction range from some methane to high molecular weight paraffinic waxes containing more than 50 carbon atoms.

Numerous catalysts incorporating active metals, such as iron, cobalt, ruthenium, rhenium, etc. have been used in carrying out the reaction and both saturated and unsaturated hydrocarbons can be produced. The synthesis reaction is very exothermic temperature sensitive whereby temperature control is required to maintain a desired hydrocarbon product selectivity.

The synthesis gas used in the Fischer-Tropsch reaction may be made from natural gas, gasified coal and other sources. A number of basic methods have been employed for producing the synthesis gas ("syngas") utilized as feedstock in the Fischer-Tropsch reaction. The numerous methodologies and systems that have been used to prepare synthesis gas include partial oxidation, steam reforming, auto-reforming or autothermal reforming. Both fixed and fluid bed systems have been employed.

The reforming reactions are endothermic and a catalyst containing nickel is often utilized. Partial oxidation (non-catalytic or catalytic) involves sub-stoichiometric combustion of light hydrocarbons such as methane to produce the synthesis gas. The partial oxidation reaction is typically carried out commercially using high purity oxygen.

In some situations these synthesis gas production methods may be combined to form another method. A combination of partial oxidation and steam reforming, known as autothermal reforming, wherein air may be used as the oxygen-containing gas for the partial oxidation reaction has also been used for producing synthesis gas heretofore. Autothermal reforming, the combination of partial oxidation and steam reforming, allows the exothermic heat of the partial oxidation to supply the necessary heat for the endothermic steam reforming reaction. The autothermal reforming process can be carried out in a relatively inexpensive refractory lined carbon steel vessel whereby a relatively lower cost is typically involved.

The Fischer-Tropsch process to produce paraffins and paraffin/olefin mixtures also produces a wide variety of oxygenates. These oxygenates, which include aldehydes, acids, ketones and alcohols, are detrimental in a variety of applications of these paraffins or olefins or mixtures thereof. In particular, the catalysts used to further process the paraffins and paraffin/olefin mixture to their desired end product are poisoned by oxygenates. The oxygenate content needs to be reduced from amounts on the order of about 200 to 400 parts per million in an untreated paraffin/and (or) olefins stream, down to as low as 1 part per million or lower in order for the paraffins or olefins or mixtures thereof to be processed without poisoning the adsorbent/catalyst or otherwise being detrimental in the processing of these paraffins or olefins or mixtures thereof.

There have been several different adsorption schemes proposed for removal of oxygenates from low carbon paraffins, i.e. those averaging about $C_5$. For example, in U.S. Pat. No. 6,111,162, hydrocarbons with 3 to 8 carbon atoms were treated by removal of oxygenated contaminants by an adsorbent comprising silica gel. In U.S. Pat. No. 5,427,689, a variety of polar substances, including water, alcohols, ethers, aldehydes, ketones, amines, mercaptans, organic sulfides and carboxylic acids were removed from a hydrocarbon containing 1 to 10 carbon atoms using a sorbent composition comprising aluminum borate and zirconium borate. However, heretofore, there has not been proposed a process for sufficiently removing oxygenates from the high carbon ($C_{10}$ to $C_{15}$) paraffins and paraffin/olefin mixture employed in the process of the present invention. These mixtures comprise from 0 to 50 wt-% olefins and 50 to 99.99 wt-% paraffins. There are often dozens of different oxygenate compounds found in a paraffin and paraffin/olefin mixture feed made by the Fisher-Tropsch process and it is necessary to have a general process that works to remove all the oxygenate species in order to make use of the paraffins and paraffin/olefin mixture in a wide variety of processes. Accordingly, it is the combined presence of these compounds that it is considered desirable to remove from the paraffin and paraffin/olefin mixture feed. In addition, in many applications of the present invention, it is desirable to be able to regenerate the adsorbents used to remove oxygenates from the paraffin and paraffin/olefin mixture feed. There are considerable cost savings in being able to reuse the adsorbents after regeneration of the bed, rather than frequent bed replacement.

SUMMARY OF THE INVENTION

The present invention comprises a process for removal of oxygenates from a stream comprising 50 to 99.99 wt-% paraffins and 0 to 50 wt-% olefins comprising passing a feed stream, comprising one or more $C_{10}$ to $C_{15}$ feed paraffins and olefins mixture and one or more oxygenates through an adsorbent bed to remove essentially all of the oxygenates; and recovering the paraffins and the olefins, when present. The level of oxygenates is below the level that is detectable with standard laboratory procedures, such as gas chromatography. In some embodiments of the present invention, it is considered necessary to send the paraffin-rich stream through a second adsorbent bed comprising a molecular sieve in order to insure completion of removal of the oxygenate impurities. Typically, a 5A polishing bed is used to complete their removal from the paraffin-rich stream. This invention is particularly useful in purifying the feed streams for certain reactions. Trace amounts of oxygenates can have detrimental effects upon an adsorbent/catalyst. Among the processes that are improved by the removal of oxygenates in accordance with the present invention are the dehydrogenation of normal paraffins to olefins and processes for separating normal paraffins from branched and cyclic hydrocarbons. In the case where the feed is a mixture of paraffins and olefins, this stream is suitable for direct alkylation with benzene after oxygenate removal treatment prior to forming alkylated benzene. Accordingly, one embodiment of the present invention comprises a process for dehydrogenation of normal paraffins to olefins comprising first passing a paraffin stream comprising $C_{10}$ to $C_{15}$ paraffins through at least one adsorbent bed comprising one or more adsorbents selected from the group consisting of silica gel, activated alumina and alkaline or alkaline earth cation exchange X-zeolite wherein the adsorbents remove essentially all oxygenates from the paraffin stream by adsorption, and then passing the paraffin stream to a reactor containing a dehydrogenation catalyst to convert at least a portion of the paraffin stream to olefins. Another embodiment of the present invention comprises a process comprising first passing a paraffin stream comprising $C_{10}$ to $C_{15}$ paraffins through at least one adsorbent bed comprising one or more adsorbents selected from the group consisting of silica gel, activated alumina and alkaline or alkaline earth cation exchange X-zeolite wherein the adsorbents remove essentially all oxygenates from the paraffin stream by adsorption, and then passing the paraffin stream to an adsorbent bed comprising a molecular sieve to separate n-paraffins from the paraffin stream.

Another embodiment of the present invention comprises a process comprising of first passing the stream comprising 50 to 99.99% $C_{10}$ to $C_{15}$ paraffins and 0 to 50% olefins through at least one adsorbent bed comprising one or more adsorbents selected from the group consisting of silica gel, activated alumina and alkaline or alkaline earth cation exchange X-zeolite wherein the adsorbents remove essentially all oxygenates from the stream by adsorption, and then combining the stream with benzene and passing the resulting alkylation stream to a reactor containing a alkylation catalyst to convert at least a portion of the olefins to alkylated benzene.

DETAILED DESCRIPTION OF THE INVENTION

Figure 1:
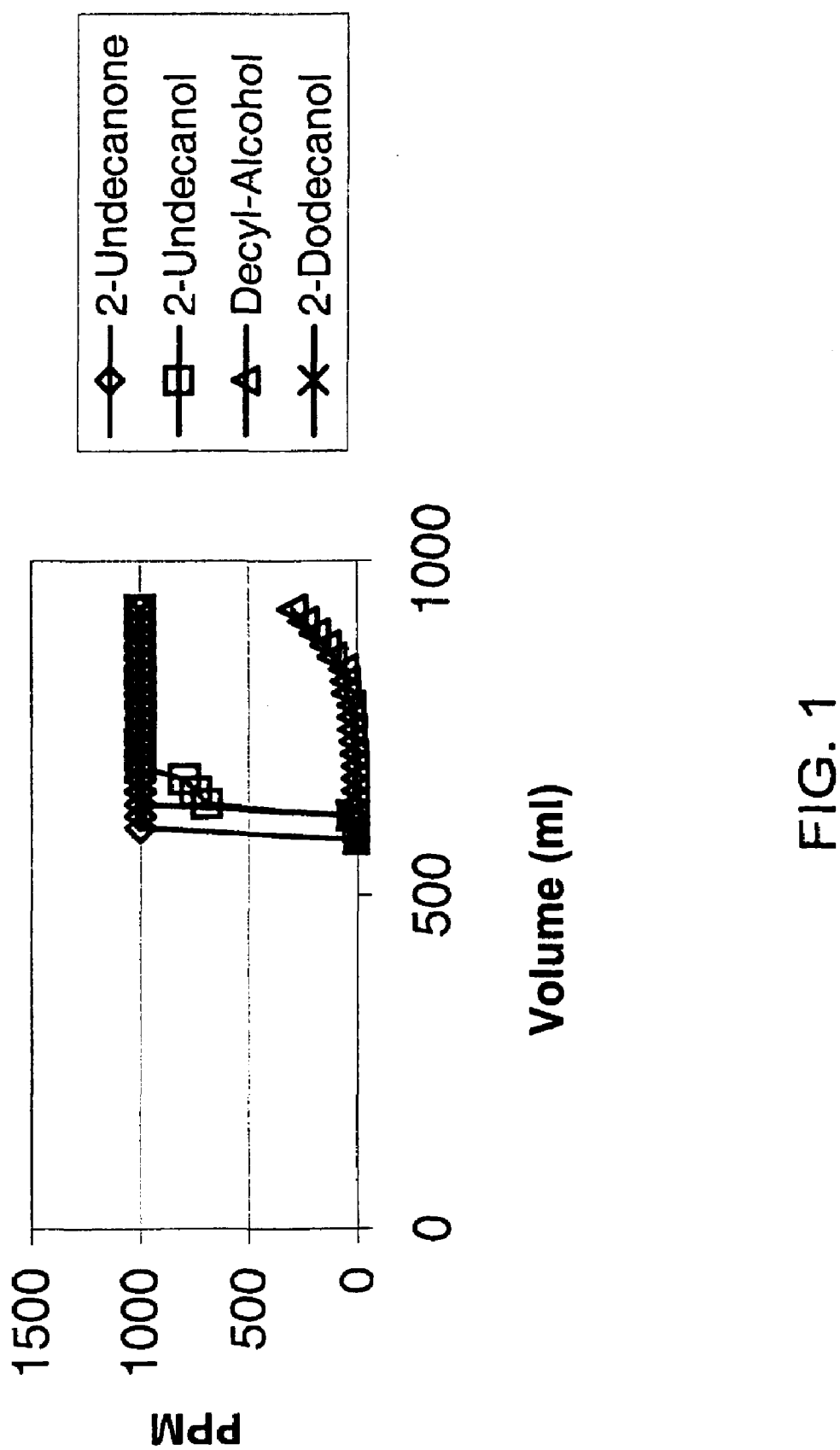
FIG. 1 shows a feed breakthrough in alumina adsorbent of 1000 ppm each of 2-undecanone, 2-undecanol, decyl alcohol, lauric acid, and 2-dodecanol.

The present invention comprises a process for removal of oxygenates from a paraffin and olefin mixture or a paraffin-rich stream which comprises passing a feed stream, comprising one or more $C_{10}$ to $C_{15}$ feed paraffins or paraffin and olefin mixture and one or more oxygenates through an adsorbent bed to remove essentially all of the oxygenates; and recovering the paraffins or paraffin and olefin mixture. Typically, the paraffin and olefin mixture referred to herein as olefin-rich streams will comprise up to 50 wt-% olefin with the remainder comprising paraffins, plus impurities. Up to 1% of the paraffin and olefin mixture or paraffin-rich streams will comprise the oxygenate impurities to be removed by the present invention. In the paraffin-rich streams, the streams typically comprise about 99 wt-% paraffins and sometimes up to 99.99 wt-% paraffins. In such a typical paraffin-rich or olefin-rich paraffin stream produced in a gas to liquid Fisher-Tropsch process, it has been found that numerous hydrocarbon oxygenates are produced, including alcohols, aldehydes, ketones and acids. It is necessary to use a process to remove virtually all the oxygenates in order to employ these paraffins or olefin-rich paraffins without poisoning the adsorbent/catalyst that is used in such processes as conversion of paraffins to olefins, alkylation of olefins with benzene, and in separation of n-paraffins from other paraffins. Table 1 illustrates the extensive list of oxygenates found in three samples of paraffins or olefin-rich paraffins prior to treatment by the process of the present invention, all of which are removed by the process of the present invention. All numbers are in parts per million.

TABLE 1

| Compound | Feed 1 | Feed 2 | Feed 3 |
| --- | --- | --- | --- |
| 1-Nonanol | 1.6 | 12.1 | 3.6 |
| 2-Nonanol | <0.4 | 1.6 | 1.8 |
| 1-Decanol | 2.2 | 14.0 | 12.1 |
| 2-Decanol | 0.4 | 4.5 | 3.3 |
| 3-Decanol | <0.4 | <0.4 | 9.2 |
| 4-Decanol | 0.3 | 4.2 | 3.1 |
| Unk C10 Alcohols | <0.4 | <0.4 | <0.4 |
| 1-Undecanol | 1.6 | 9.0 | 4.3 |
| 2-Undecanol | 1.4 | 4.5 | 3.9 |
| 3-Undecanol | 0.9 | 3.3 | 4.8 |
| 4-Undecanol | 0.6 | 2.1 | 5.2 |
| Unk C11 Alcohols | 0.8 | 3.2 | 5.7 |
| 1-Dodecanol | 0.5 | 1.0 | 1.4 |

TABLE 1-continued

| Compound | Feed 1 | Feed 2 | Feed 3 |
|---|---|---|---|
| 2-Dodecanol | 4.6 | 8.0 | <0.4 |
| Unk C12 Alcohols | 6.0 | 15.3 | <1.0 |
| 1-Tridecanol | <0.4 | <0.4 | <0.4 |
| Unk C13 Alcohols | 3.1 | 6.7 | <0.4 |
| 1-Tetradecanol | <0.4 | <0.4 | <0.4 |
| Unk C14 Alcohols | 1.0 | 0.5 | <0.4 |
| 1-Octanal | 4.5 | 4.9 | 4.3 |
| 1-Nonanal | 4.2 | 6.7 | 7.7 |
| 1-Decanal | 3.9 | 8.3 | 16.9 |
| 1-Undecanal | 3.0 | 7.2 | 17.1 |
| 1-Dodecanal | <0.6 | 1.4 | <1.0 |
| 1-Tridecanal | <0.5 | <0.5 | <1.0 |
| 2-Heptanone | 0.7 | 1.6 | <0.4 |
| 2-Octanone | 1.5 | 3.8 | <0.4 |
| 2-Nonanone | 2.4 | 6.6 | 0.6 |
| 2-Decanone | 3.1 | 10.1 | 2.9 |
| 2-Undecanone | 3.3 | 11.3 | 3.5 |
| 2-Dodecanone | 1.6 | 5.7 | 1.0 |
| Unk C11 Ketones | 2.2 | 1.0 | 5.2 |
| Unk C12 Ketones | 1.3 | 5.4 | 6.1 |
| Butanoic Acid | 3.3 | 1.2 | 1.6 |
| Pentanoic Acid | 6.7 | 2.4 | 1.6 |
| Hexanoic Acid | 10.4 | 3.6 | 3.3 |
| Heptanoic Acid | 12.8 | 4.5 | 4.3 |
| Octanoic Acid | 14.3 | 4.7 | 6.7 |
| Nonanoic Acid | 16.0 | 5.3 | 9.4 |
| Decanoic Acid | 16.7 | 5.1 | 10.1 |
| Undecanoic Acid | 12.0 | 4.0 | 15.4 |
| Lauric Acid | 6.6 | 2.4 | 12.6 |

Table 2 shows a summary of the types of oxygenates found in the feed.

TABLE 2

| Compound | Feed 1 | Feed 2 | Feed 3 |
|---|---|---|---|
| Alcohols | 25.0 | 90.0 | 58.4 |
| Aldehydes | 15.6 | 28.5 | 46.0 |
| Ketones | 12.6 | 39.1 | 8.0 |
| Acids | 98.8 | 33.2 | 65.0 |

In the practice of the present invention, a paraffin-rich or olefin-rich paraffins stream is first passed though an adsorbent bed containing at least one adsorbent selected from the group consisting of silica gel, activated alumina and alkaline or alkaline earth cation exchange X-zeolite. The X-zeolite has a $Si/Al_2$ ratio from about 2.0 to 3.0. An X-zeolite having a $Si/Al_2$ ratio of 2, 2.3 or 2.5 is preferred.

In addition to removal of oxygenates, in some embodiments of the present invention, it is necessary to remove compounds containing other elements from Group VIB of the Periodic Table of the Elements. In particular, when a lower quality gas well condensate is used that contains up to 0.7 wt-% mercaptans, sulfides and disulfides, it is highly desirable to process this stream to reduce the sulfur compound level below 5 wppm that is detrimental to the platinum catalyst used to make LAB. The sulfur compounds may be removed by use of adsorbents known to one of ordinary skill in the art. Advantageous results can be found using an adsorbent bed comprising ADS-102, PEP adsorbent available from UOP LLC, Des Plaines, Ill.

The adsorbent bed may be exclusively dedicated to treating the paraffin-rich or olefin-rich paraffins stream or it may be integrated with a chemical conversion process that uses the paraffins stream to effect other separations. A dedicated adsorbent bed is one where essentially its sole purpose is to remove oxygenates from the paraffins stream regardless of whether only the paraffins stream passes through it or the paraffins stream is combined with a chemical conversion process stream and the combined stream passes through the bed. In an integrated adsorbent bed, the paraffins stream and a process stream are combined and the adsorbent bed serves to remove at least one component in the process stream. For example, in processes for alkylation process for making alkyl benzenes from paraffins, paraffins are dehydrogenated, and the dehydrogenation stream is typically passed through an adsorbent bed such as zeolite 13x to remove undesirable aromatics. In such processes, the paraffins stream is preferably fed to the process after dehydrogenation and prior to the adsorption of water and aromatics in the adsorption bed.

When dedicated, the adsorbent bed is typically operated at a temperature between 25 to 60° C. and preferably is operated slightly above ambient (40° C.). While this adsorbent bed has been found to reduce the level of oxygenates below the level that is measurable by gas chromatography, since it has been found that under some conditions these adsorbent beds become less efficient over time in removal of the oxygenates further measures are needed to insure that all oxygenates are removed. Accordingly, in the preferred embodiments of the invention, a second adsorbent bed operating at an elevated temperature between about 150° and 200° C. containing a 5A adsorbent has been found to remove any residual oxygenates not removed by the first bed. Adsorbent beds that are integrated with a process using the paraffin-rich or olefin-rich paraffins stream are generally operated under conditions suitable for the process.

After the adsorbent beds have reached their capacity for removal of oxygenates from paraffin-rich streams, a regeneration procedure is followed to remove the adsorbed oxygenates from the adsorbent bed. A gas or liquid is sent through the bed, which is maintained at an elevated temperature for a sufficient period of time for the bed to be rejuvenated through the removal of the oxygenates. In one embodiment of the rejuvenation process, nitrogen was used as the regenerant gas at 3000 GHSV, the bed was first heated to 130° C. for two hours and then the temperature increased to 250° C. for three more hours. Other regenerant gases or liquids may be used, such as available process streams. The bed may also be regenerated in accordance with the procedure set forth in U.S. Pat. No. 6,225,518 B1, incorporated herein by reference in its entirety. Usually, due to the low concentration of oxygenates, the integrated adsorbent bed is regenerated or replaced based upon its performance in the process.

EXAMPLE

Figure 2:
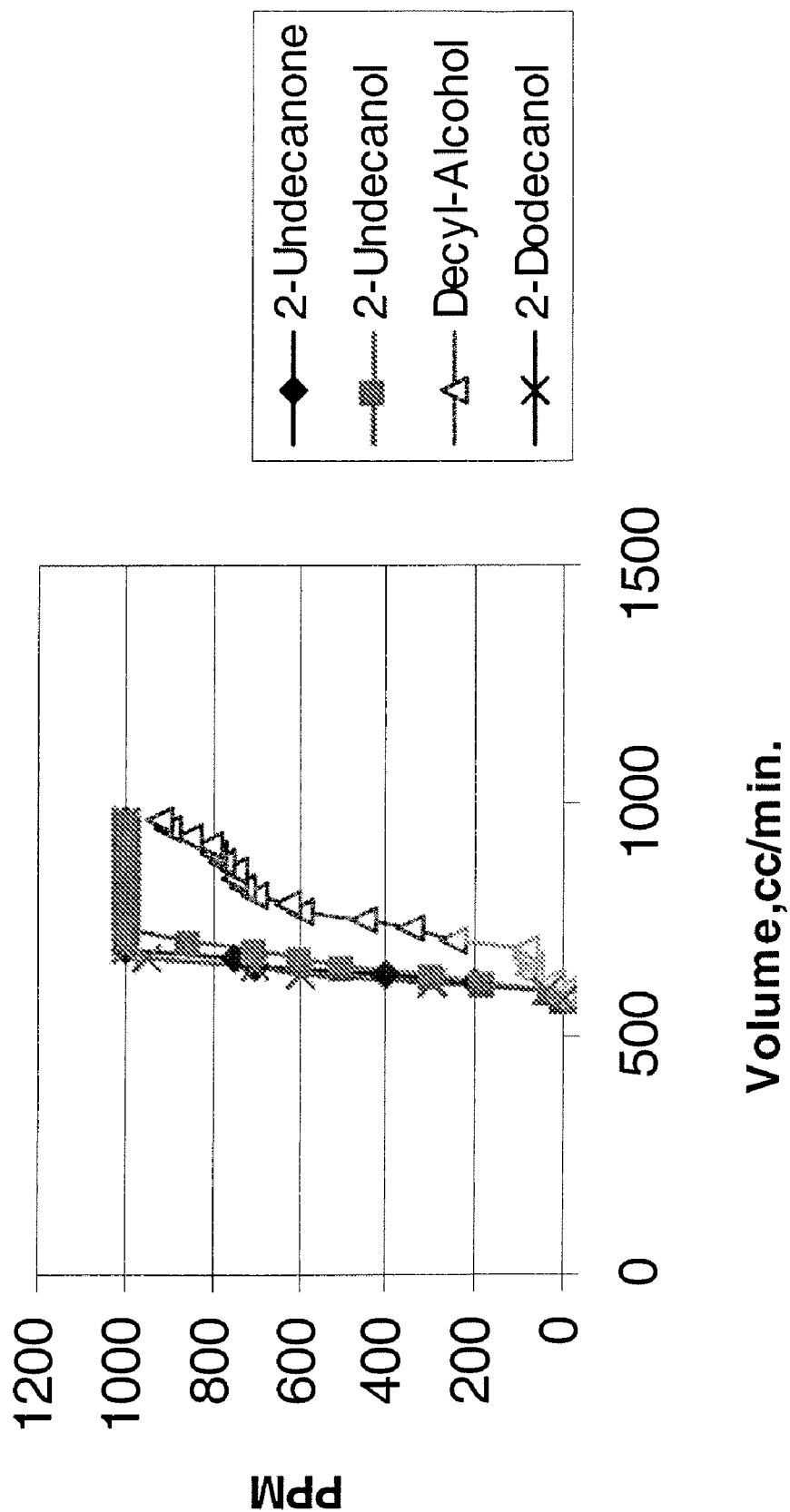
FIG. 2 shows a feed breakthrough in a silica gel adsorbent of 1000 ppm each of 2-undecanone, 2-undecanol, decyl alcohol, lauric acid, and 2-dodecanol.
Figure 3:
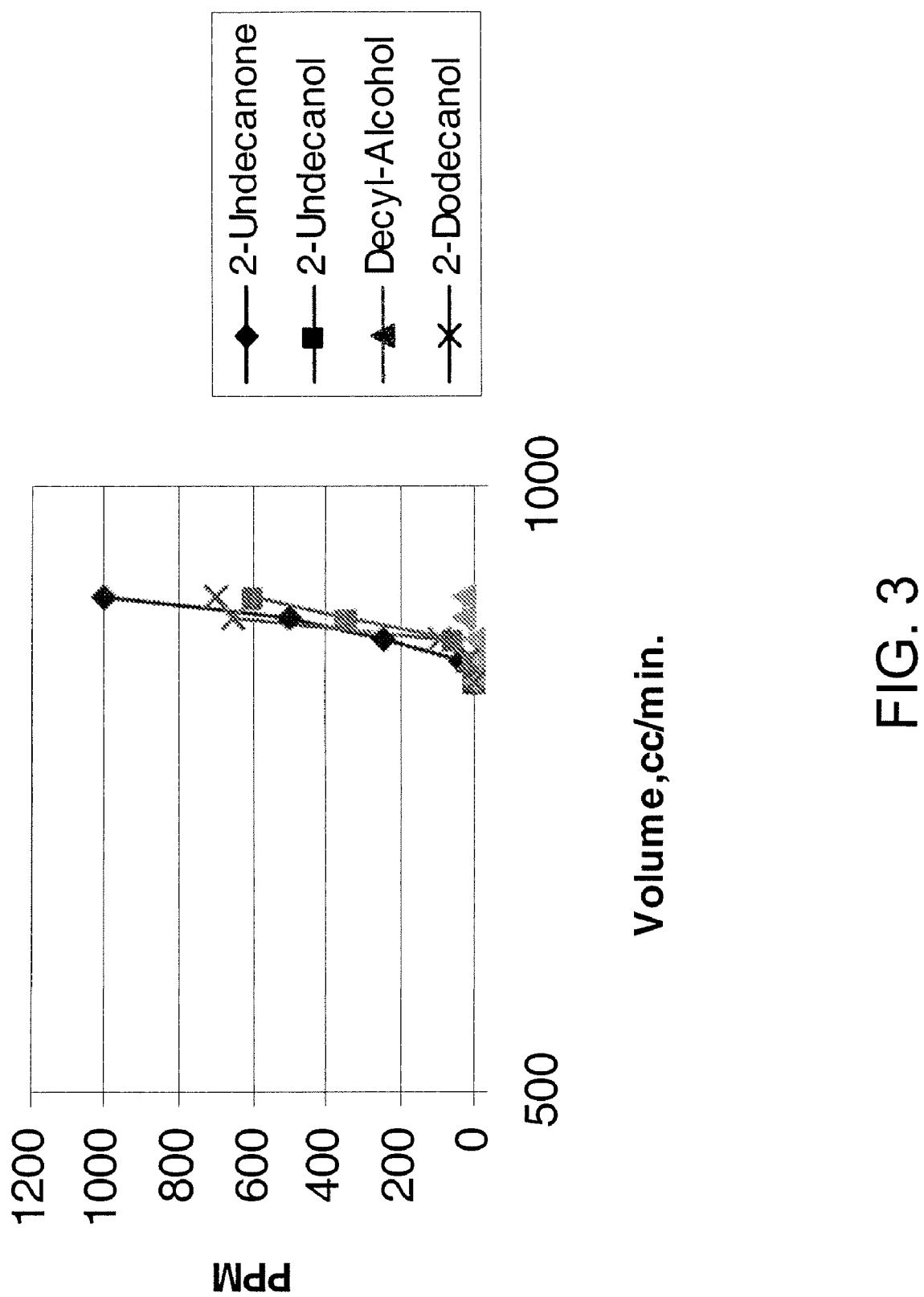
FIG. 3 shows a feed breakthrough in a different silica gel adsorbent of 1000 ppm each of 2-undecanone, 2-undecanol, decyl alcohol, lauric acid, and 2-dodecanol.
Figure 4:
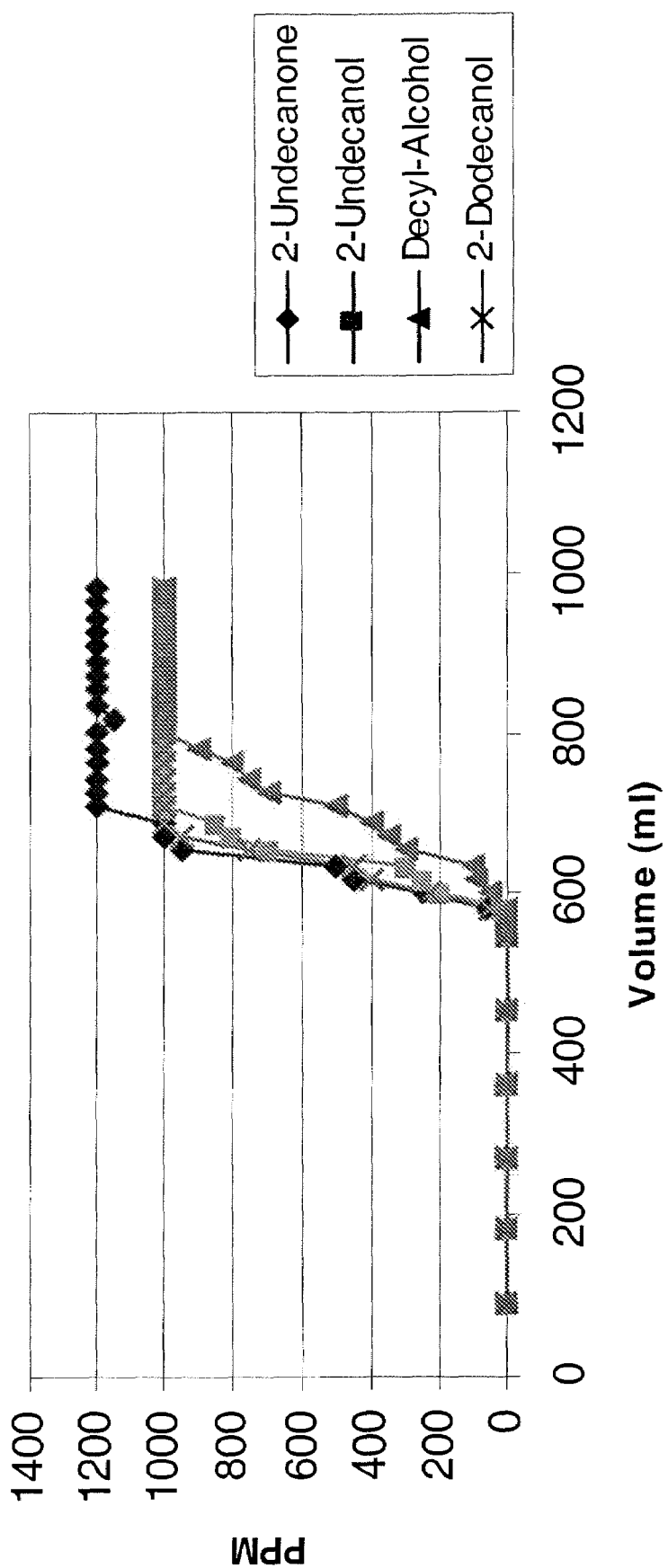
FIG. 4 shows a feed breakthrough of a 13× adsorbent of 1000 ppm each of 2-undecanone, 2-undecanol, decyl alcohol, lauric acid, and 2-dodecanol.

Laboratory tests have been made determine the extent of oxygenate removal from hydrocarbons. The process is carried out in a 20 ml stainless steel column. The column is installed in an enclosed box and is packed with 20 ml of adsorbent. Initially, the temperature of the enclosed box is raised to the desired temperature, which was 40° C. in this example. After stabilizing the temperature, oxygenate-containing hydrocarbon feed is introduced with a flow rate of 4 LHSV. The effluent is collected and analyzed for the oxygenate impurities. The feed that was tested contained 1000 ppm each of five typical kerosene containing oxygenates: 2-undecanone, 2-undecanol, decyl alcohol, lauric acid, and 2-dodecanol. Very sharp breakthroughs were noted with alumina, silica gel, and sodium X types of adsorbents. In FIG. 1, the alumina tested as an adsorbent was a spherical promoted alumina, sold by UOP LLC, Des Plaines, Ill. as 9139A activated alumina. The adsorbent had a capacity of 21.95 wt-%. In FIG. 2, the adsorbent was Eagle 32-950 silica gel, sold by Eagle Chemical Co, Inc., Mobile, Ala. The adsorbent had a capacity of 19.76 wt-%. In FIG. 3, the adsorbent used was silica gel Grace 408, sold by W. R. Grace, Grace Davison division, Columbia, Md. The adsorbent had a capacity of 32.33 wt-%. In FIG. 4, Molsiv adsorbent MRG-E is used and is sold by UOP, Des Plaines, Ill. The adsorbent had a capacity of 23.57 wt-%. Each of the figures shows the substantial capacity of these adsorbents for the oxygenates, along with a sharp breakthrough after the capacity of the adsorbent has been achieved. Also, it is noted that lauric acid is strongly adsorbed by the adsorbent in all four cases.

What is claimed is:

1. A process for dehydrogenation of normal paraffins to olefins comprising first passing a stream comprising $C_{10}$ to $C_{15}$ paraffins and up to 50 wt% olefins through at least one adsorbent bed comprising one or more adsorbents selected from the group consisting of alkaline or alkaline earth cation exchange X-zeolite wherein said adsorbents remove essentially all oxygenates from said paraffin stream by adsorption, and then passing said paraffin stream to a reactor containing a dehydrogenation catalyst to convert at least a portion of said stream to olefins.

2. The process of claim 1 wherein after said stream passes through said adsorbent bed, said stream is sent to a second adsorbent bed comprising 5A zeolite adsorbent to further remove oxygenates.

3. The process of claim 1 wherein said adsorbent beds are regenerated at a predetermined time to remove at least a portion of said oxygenates adsorbed onto said adsorbents.

* * * * *